United States Patent [19]

Turner, Sr.

[11] Patent Number: Plant 5,378

[45] Date of Patent: Dec. 25, 1984

[54] *NERIUM OLEANDER* PLANT—TURNER'S SHARI D

[76] Inventor: Ted L. Turner, Sr., 6503 S. Padre Island Dr., Corpus Christi, Tex. 78412

[21] Appl. No.: 498,113

[22] Filed: May 25, 1983

[51] Int. Cl.[3] ..... A01H 5/00

[52] U.S. Cl. ..... Plt./54

[58] Field of Search ..... Plt./54

*Primary Examiner*—Robert E. Bagwill

*Attorney, Agent, or Firm*—Stewart N. Rice

[57] ABSTRACT

A *Nerium oleander* plant which has a full and upright habit of fairly rapid growth, being particularly characterized by the unique color of its inflorescence, the flowers being a soft buff yellow color with tinges of pink.

1 Drawing Figure

DESCRIPTION OF THE INVENTION

The present invention relates to a new and distinct variety of *Nerium oleander* which was originated by me as a seedling by successive selection and crossing. I originally started from a *Nerium oleander* "Mrs. Roeding" and a *Nerium oleander* "Petite salmon". The "Mrs. Roeding" produces a salmon pink semi-double flower, the plant being semi-dwarf, that is about eight feet tall at maturity. The "Petite salmon" produces single flowers which are bright salmon pink in color, and is a dwarf plant about six feet high at maturity. However in making my crosses, I observed that pollination was sometimes accomplished by bees from unknown plants. Thus unknown parentage could have been introduced by the bees even though I did not purposely introduce any parentage other than the "Mrs. Roeding" and the "Petite Salmon".

The new and distinct variety of *Nerium oleander* claimed by me herein was developed through several generations of selection and crossing. From one group of seedlings I observed a plant, being the plant claimed herein, having a new and distinct color of flowers, and from cuttings of such flower I was able to asexually reproduce plants having the same characteristics and flower color as the original seedling. All of the descendant plants showed the same characteristics as the original seedling, and as a result of extensive observations and tests which are not described in full herein for sake of brevity, it is my opinion and I am convinced that my new plant is a new variety of *Nerium oleander* which is distinguished from all other varieties of which I am aware as evidenced by the following unique combination of principal characteristics which are outstanding therein:

(1) An upright habit of fairly rapid growth making it especially suitable as a screening plant;

(2) An ability to be asexually reproduced;

(3) The ability to flower off and on throughout the year;

(4) The ability to produce a flower having a soft buff yellow color with tinges of pink.

Asexual reproductions of my new variety as by cuttings show that the foregoing characteristics and distinctions come true to form and are established and transmitted through succeeding propagations.

The accompanying FIGURE is a photograph of a typical flower on the plant of my new variety more clearly illustrating the colors present on each flower.

The true color of the foliage and flowers is described in the following description and is depicted in the FIGURE which depicts the color as nearly as true as is reasonably possible in a color illustration of this type.

The following is a detailed description of my new variety of *Nerium oleander,* with color numbers in accordance with the Pantone Matching System of colors for printing inks, 16th edition, published by Pantone, Inc., 1977. Terms used the describe colors are those of ordinary significance.

THE PLANT

Growth habit: Upright, full size; the height of an unpruned mature plant will probably be from about 4 to 6 meters, but has not yet been determined; fast growing. The plant grows full from just about ground level upward, with the width of the plant about 30% to 60% of the height.

Hardiness: Adapted to seaside planting as it tolerates soil with relatively high salt content; tolerates droughts; will not withstand prolonged and severe freezing weather; most suitable for the Southern United States from California to Florida, in the areas known as Zones 9 and 10; withstands heat and light and grows best in full sun.

Branches: The plant is loosely branched from just above ground level with main branches and branchlets ascending. The plant does not develop a central leader or trunk. New growth of branches is medium green, Color No. 383U, changing to light brown in color as branches mature.

Blooming period: Blooms off and on the entire year.

THE FOLIAGE

Type: Broadleaf evergreen; numerous; petioled; grow in a whorl with three leaves in each whorl.

Shape: Linear-lanceolate, with entire margins. Apex is more or less acuminate and slightly non-symmetrical, and base is acute.

Petioles: Lengh, from about 4 to 6 mm; color pale green.

Leaf size: length of mature leaf from about 150 to 200 mm; width of mature leaf about 20 to 30 mm. Size of leaf varies according to sunshine conditions at the time the leaf is produced, with larger leaves being produced under cloudy conditions than under sunny conditions.

Venation: Midrib on under surface prominent and readily apparent and is pale green, Color No. 587U; on upper surface midrib is clearly visible and slightly recessed, and is pale green, Color No. 587U; lateral veins are not readily apparent on upper surface but under surface contains numerous, delicate, almost parallel lateral veins which are readily apparent, the lateral veins being substantially perpendicular to the midrib.

Leaf color: Mature leaves: upper surface — dark green, Color No. 574C; under surface much lighter in color than upper surface, being a medium green, Color No. 582U.

New leaves: About the same color as mature leaves but perhaps slightly lighter in color.

Leaf texture: Tough, leathery; smooth; upper surface—semi-glossy; lower surface — dull.

THE INFLORESCENCE

Position and abundance: Flowers cluster at twig or branch ends in terminal cymes, with cymes appearing at various positions from the lower part to the upper part of the plant.

Form: Single; regular; pediceled; petals united in a sympetalous corolla; salverform; tube spreads into five limbs or lobes; each flower is about 50 to 65 mm across; corona conspicuous at junction of tube and spreading limb, corona about 15 to 20 mm in diameter and much shorter than spreading limbs, the corona having five crownlike appendages, each appendage corresponding to a limb, each appendage being 3 to 5 toothed.

Buds: Limbs convolute in the bud, obliquely apiculate, the folds twisting counterclockwise when viewing down onto the tip of the bud.

Calyx: Of 5 persistent sepals, imbricate in the bud, lanceolate, acuminate, about 5 to 7 mm long.

Stamen: 5 stamens; filaments partly adnate to corolla tube; anthers with 2 basal tails, apex long-attenuate, hairy.

Pistal: Styles united, slender, stigma simple, ovary superior.

Color of flower: Limbs of the corolla in new flowers are soft buff yellow color, Color No. 155C, except that one edge of the margin of each limb (as viewed from the topside of the flower) is tinged with medium pink, Color 204U, the edge of each limb that is tinged with pink being that edge which is exposed in the bud. As the flowers age, the color of the limbs fade somewhat becoming more pale than in the new growth. The corona is pale golden yellow, Color 113U, with 5 groups of 3 dark pink streaks, Color 206U, each group of pink streaks consisting of a thicker central streak having a narrower streak on each side, each group of pink streaks being more to less centered with and corresponding to limb and to a said corona appendage, the streaks being radial in nature (as opposed to circular) such that the streaks extend from the edge of each appendage down into the corona tube, or vice versa. The outside of the corolla tube of each flower is very pale coral pink, Color No. 162U, with tinges of pale yellow, Color No. 113U, there being in particular 5 small pale yellow streaks extending along the tube alternate with the spreading limbs. The calyx and sepals are light green, Color No. 382U.

Color of buds: Very pale coral pink, Color No. 162U, with 5 spiraling medium pink streaks, Color No. 204U, corresponding to edges of the convoluted limbs.

To further describe my new variety of *Nerium oleander,* it is very similar in size and growth habit to the other well-known full size *Nerium oleanders* which grow in an upright manner, except for the color of the flowers. I am not aware of any *Nerium oleander* having a flower which is the same as that produced by my plant. I am aware of an oleander having canary yellow "single" flowers, however the color of the flowers of my new variety are much paler yellow.

There is also a variety of oleander having "double" flowers which are a buff yellow, which is much duller than the color of the flowers of my new variety; and, the flowers of my variety are "singles" as opposed to "doubles". My new variety also differs from the prior art in that it is in bloom about 75% of the time whereas prior art oleanders are in bloom only about 40% to 50% of the time.

VARIETY NAME

The proposed variety name of my new plant is *Nerium oleander* "Turner's Shari D".

I claim:

1. A new and distinct variety of *Nerium oleander* substantially as shown and described, having an upright habit of fairly rapid growth making it especially suitable as a screening plant, having an ability to be asexually reproduced, having the ability to flower off and on throughout the entire year, and being particularly characterized by the unique color of its inflorescence, the flowers being a pale buff yellow color with tinges of pink.

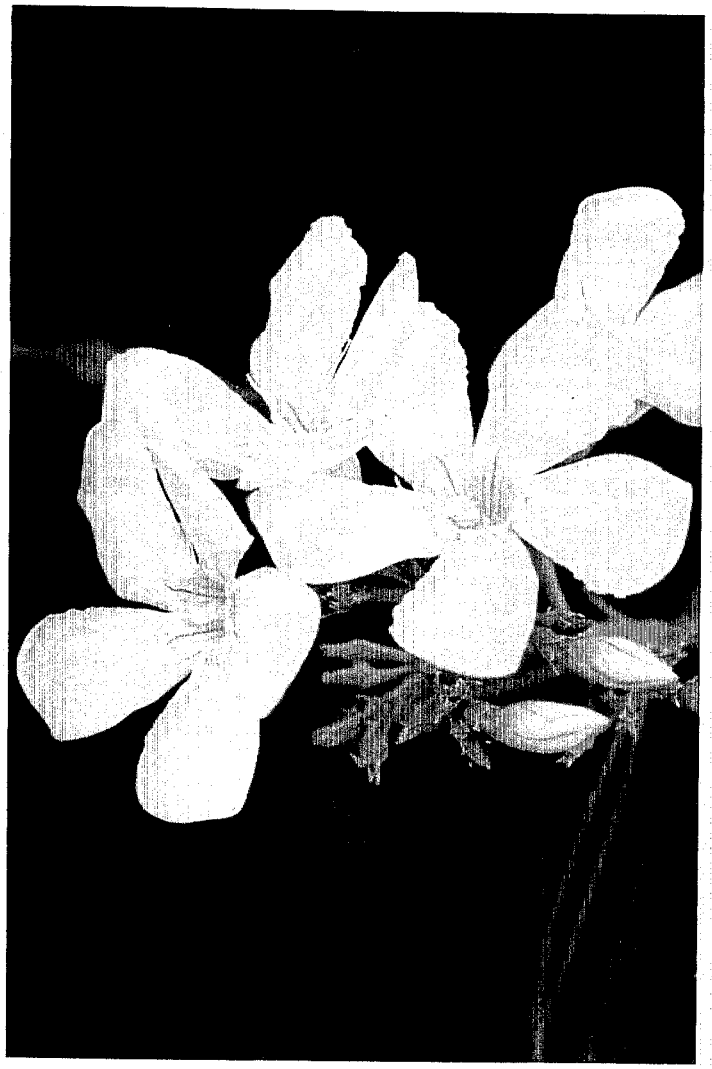

* * * * *